United States Patent
Ovchinnikov et al.

(10) Patent No.: US 8,956,320 B2
(45) Date of Patent: Feb. 17, 2015

(54) CAPILLARY VALVE

(75) Inventors: Mikhail A. Ovchinnikov, Dana Point, CA (US); Satish Yalamanchili, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 319 days.

(21) Appl. No.: 13/596,314

(22) Filed: Aug. 28, 2012

(65) Prior Publication Data

US 2014/0066832 A1    Mar. 6, 2014

(51) Int. Cl.
*A61M 5/00* (2006.01)

(52) U.S. Cl.
USPC ............... 604/9; 239/34; 239/50; 604/131; 604/247; 604/8; 137/14

(58) Field of Classification Search
CPC .................................................. A61F 9/00781
USPC .............. 604/9, 8, 890.1, 131, 132, 247, 246; 239/34, 50; 137/14
See application file for complete search history.

(56) References Cited

U.S. PATENT DOCUMENTS

| | | | |
|---|---|---|---|
| 6,383,218 B1* | 5/2002 | Sourdille et al. | 623/4.1 |
| 2011/0105986 A1* | 5/2011 | Bronstein et al. | 604/8 |
| 2011/0270216 A1* | 11/2011 | Rykhus et al. | 604/500 |
| 2013/0261530 A1* | 10/2013 | Yalamanchili | 604/9 |

* cited by examiner

*Primary Examiner* — Philip R Wiest
*Assistant Examiner* — Ariana Zimbouski
(74) *Attorney, Agent, or Firm* — Kenneth D. Bassinger

(57) ABSTRACT

A capillary fluid flow valve may include a chamber having a first boundary surface and a second boundary surface defined by a housing. The first and second boundary surfaces may be spaced apart by a gap sized to invoke capillary action between the surfaces. The first surface may be angled relative to the second surface. The chamber may have an inlet port, an outlet port, and an air vent port. The gap at the air vent port may be smaller than the gap at the outlet port and the gap at the outlet port may be smaller than the gap at the inlet port.

8 Claims, 6 Drawing Sheets

CAPILLARY VALVE

BACKGROUND

The present disclosure relates generally to capillary valves and more particularly, to capillary valves and associated systems for use in ophthalmic treatments.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye that helps to explain the processes of glaucoma. In FIG. 1, representations of the lens 10, cornea 20, iris 30, ciliary body 40, trabecular meshwork 50, Schlemm's canal 60, and anterior chamber 70 are pictured. Anatomically, the anterior segment of the eye includes the structures that cause elevated IOP which may lead to glaucoma. Aqueous humor fluid is produced by the ciliary body 40 which lies beneath the iris 30 and adjacent to the lens 10 in the anterior segment of the eye. This aqueous humor washes over the lens 10 and iris 30 and flows to the drainage system located in the angle of the anterior chamber 70. The angle of the anterior chamber 70, which extends circumferentially around the eye, contains structures that allow the aqueous humor to drain. The trabecular meshwork 50 is commonly implicated in glaucoma. The trabecular meshwork 50 extends circumferentially around the anterior chamber 70. The trabecular meshwork 50 seems to act as a filter, limiting the outflow of aqueous humor and providing a back pressure that directly relates to IOP. Schlemm's canal 60 is located beyond the trabecular meshwork 50. Schlemm's canal 60 is fluidically coupled to collector channels (not shown) allowing aqueous humor to flow out of the anterior chamber 70. The two arrows in the anterior segment of FIG. 1 show the flow of aqueous humor from the ciliary bodies 40, over the lens 10, over the iris 30, through the trabecular meshwork 50, and into Schlemm's canal 60 and its collector channels.

One method of treating glaucoma includes implanting a Glaucoma Drainage Device (GDD) in a patient's eye. The GDD allows fluid to flow from the interior chamber of the eye to a drainage site, relieving pressure in the eye and thus lowering IOP. In order to provide desired treatments to patients, it may be important to regulate the drainage flow through the GDD. However, some implantable GDDs suffer from the poor IOP control due to the absence of flow resistance or the unpredictable functioning of their valves.

The system and methods disclosed herein overcome one or more of the deficiencies of the prior art.

SUMMARY

In one exemplary aspect, the present disclosure is directed to a capillary fluid flow valve. The valve may include a chamber having a first boundary surface and a second boundary surface defined by a housing. The first and second boundary surfaces may be spaced apart by a gap sized to invoke capillary action between the surfaces. The first surface may be angled relative to the second surface. The chamber may have an inlet port, an outlet port, and an air vent port. The gap at the air vent port may be smaller than the gap at the outlet port and the gap at the outlet port may be smaller than the gap at the inlet port.

In one aspect, the opposing surfaces are hydrophobic surfaces. In another aspect, the air vent port is open to atmospheric pressure. In one aspect, the chamber is substantially triangular, and the inlet port, outlet port, and air vent port are disposed at the vertices of the triangular chamber.

In another exemplary aspect, the present disclosure is directed to an implantable device for treating an ocular condition. The implantable device may be sized for implantation in an eye of a patient, and may include a drainage tube configured to extend from an anterior chamber of an eye of a patient. It may also include a capillary valve in communication with the drainage tube. The capillary valve may have a chamber with an inlet port, an outlet port, and an air vent port. The inlet port may receive fluid from the drainage tube. The chamber may be defined between a first boundary surface and a second boundary surface, with the first and second boundary surfaces being spaced apart by a distance invoking capillary action between the surfaces. The first surface may be angled relative to the second surface. The chamber may be configured to receive a liquid at the inlet port and receive air at the air vent port. The liquid and air may interface within the chamber to permit fluid to flow from the outlet port at a cracking pressure.

In one aspect, the opposing surfaces are hydrophobic surfaces. In another aspect, the air vent port is open to atmospheric pressure. In one aspect, the chamber is substantially triangular, and the inlet port, outlet port, and air vent port are disposed at the vertices of the triangular chamber.

In another exemplary aspect, the present disclosure is directed to a method of regulating fluid flow. The method may include introducing fluid to a fluid inlet port of a chamber, the chamber being defined by first and second opposing surfaces spaced apart by a distance invoking capillary action between the first and second opposing surfaces, the first surface being angled relative to the second surface. The method also may include exposing an air vent port to a gas having a gas pressure, the gas pressure opposing the capillary action of the liquid in the chamber. The method also may include draining the fluid from an outlet port when the pressure differential between the fluid pressure and the air pressure exceeds a cracking pressure placing the outlet port in liquid communication with the inlet port.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
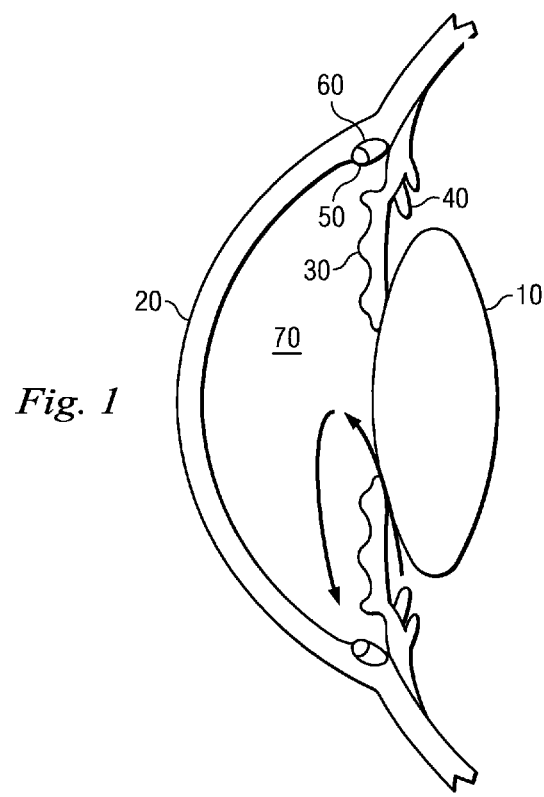
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to flow-control valve operating in part by capillary action to provide selective flow when pressure exceeds a designed threshold level. It does this because the design incorporates a water-air interface within the valve at all pressures within the working range providing an opening and closing action. Since the valve operates via capillary action and pressure differentials, the valve, in the exemplary embodiments shown, includes no moving parts. Further, the valve can be designed to open at any desired cracking pressure. As such, it is well suited for use in GDDs. Accordingly, in one aspect, the capillary valve is arranged to regulate or control the flow of drainage fluid from an anterior chamber of an eye to relive IOP. In the exemplary embodiments disclosed, the capillary valve is designed to achieve a balance of air pressure and liquid pressure to allow drainage flow between an inlet port and an outlet port in order to control the IOP of a patient.

Figure 2:
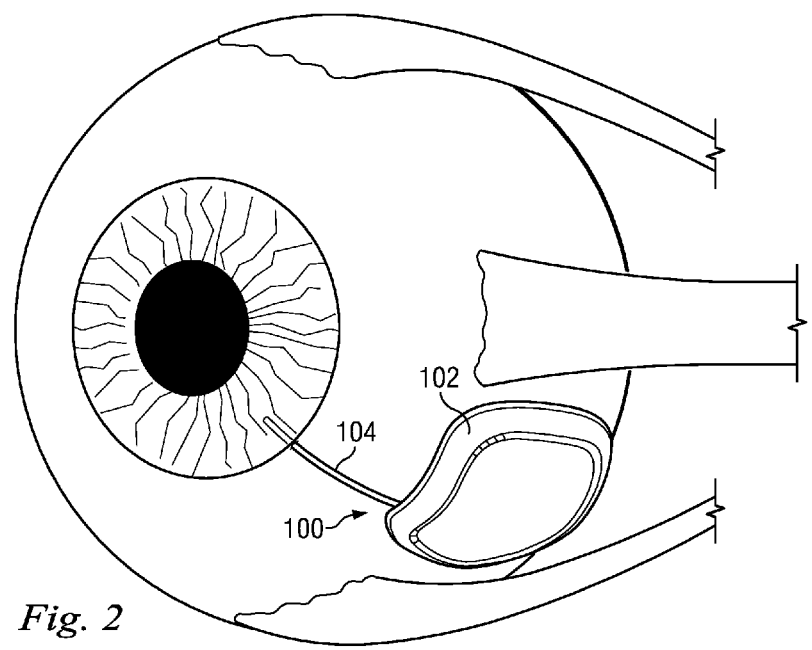
FIG. 2 is an illustration of an exemplary flow-regulating system disposed in the eye in accordance with one embodiment of the present disclosure.

FIG. 2 shows an exemplary implantable system 100 disposed on an eye to treat an ocular condition according to one exemplary aspect of the present disclosure. The implantable system 100 includes a body referred to herein as a plate 102 and a drainage tube 104 that extends from the plate 102. The plate 102 is arranged to carry various components of an IOP control system, and may include a valve, pump, transducers or sensors, a processing system and memory, drug delivery components, a power source or other components that may be used to either control the implantable system 100 or otherwise treat ocular conditions.

The plate 102 is configured to fit at least partially within the subconjunctival space and is sized for example within a range between about 15 mm×12 mm to about 30 mm×15 mm and has a thickness less than about 2 mm thick and preferably less than about 1 mm thick. The plate 102 may be formed to the radius of the eye globe (about 0.5 inches). In some embodiments, the plate 102 is rigid and preformed with a curvature suitable to substantially conform to the globe or it may be flexible to conform to the globe. Some embodiments have relatively planar outer surfaces. Some of these are small enough that conforming to the globe provides little benefit in comfort or implantation technique. The above dimensions are exemplary only, and other sizes and arrangements are contemplated. When implanted, the plate 102 may be located in the subconjunctival pocket between the conjunctiva and sclera. It may be generally located on an ocular quadrant commonly used for conventional glaucoma drainage devices with plates; that is, it may be centered such that it is equidistant from the neighboring ocular muscles that define the ocular quadrant chosen for implantation.

The drainage tube 104 is sized to bridge the anterior chamber and the plate 102 in the subconjunctival pocket to provide an auxiliary flow path for aqueous humor, bypassing the flow-resistive conventional pathway through the trabecular meshwork and shunting aqueous humor directly to a drainage site. In the example shown, the drainage tube 104 is a single tube having a single lumen. Other embodiments include a plurality of drainage tubes or a plurality of lumens cooperating together to permit fluid to flow through the implantable system 100. The drainage tube 104 is sized to extend from the plate 102 to the anterior chamber of the eye, as shown in FIG. 2. Aqueous humor may drain through the drainage tube from the anterior chamber to and out of the plate 102 to alleviate elevated intraocular pressure conditions.

Figure 3:
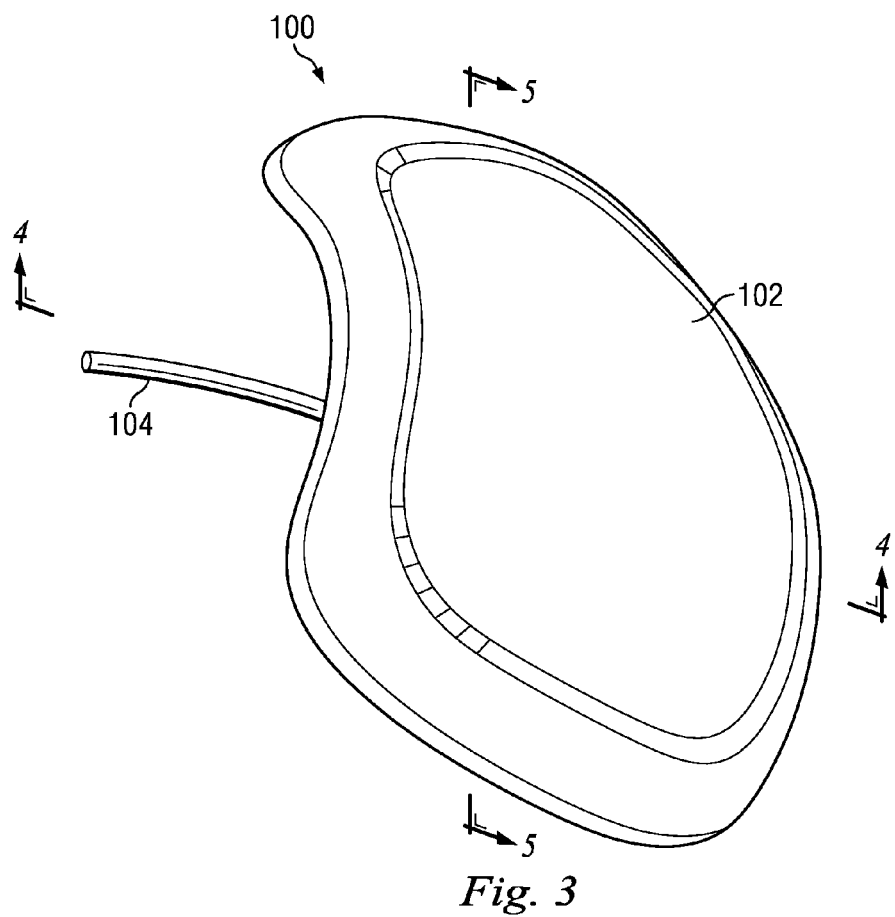
FIG. 3 is an illustration of the exemplary flow-regulating system of FIG. 2 according to the principles of the present disclosure.
Figure 4:
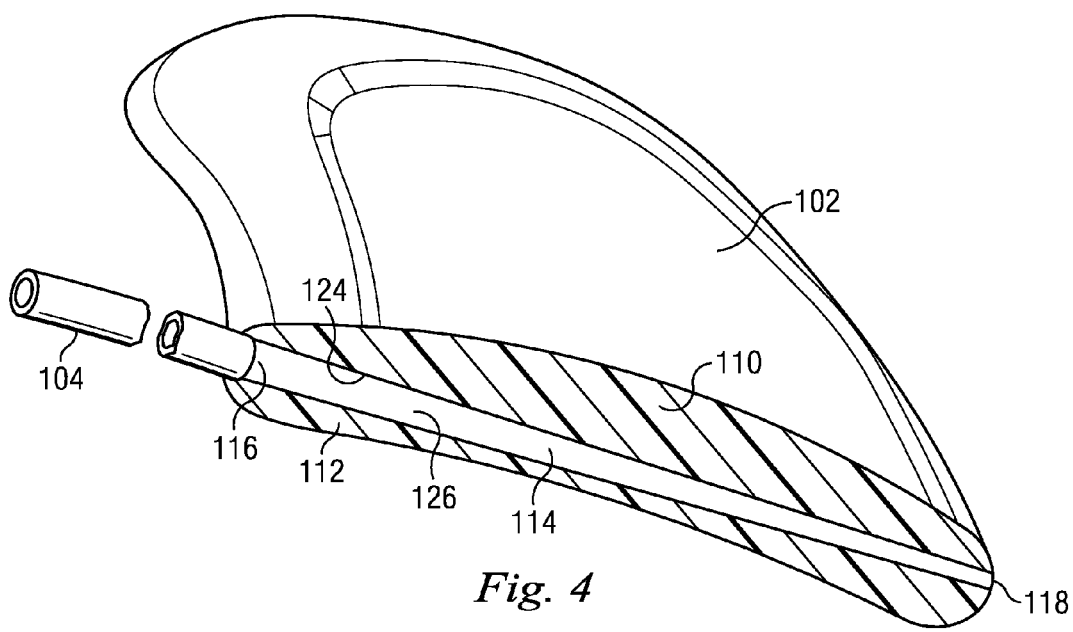
FIG. 4 is an illustration of a cross-sectional view of the flow regulating system of FIG. 3 taken along lines 4-4 in FIG. 3 according to the principles of the present disclosure.
Figure 5:
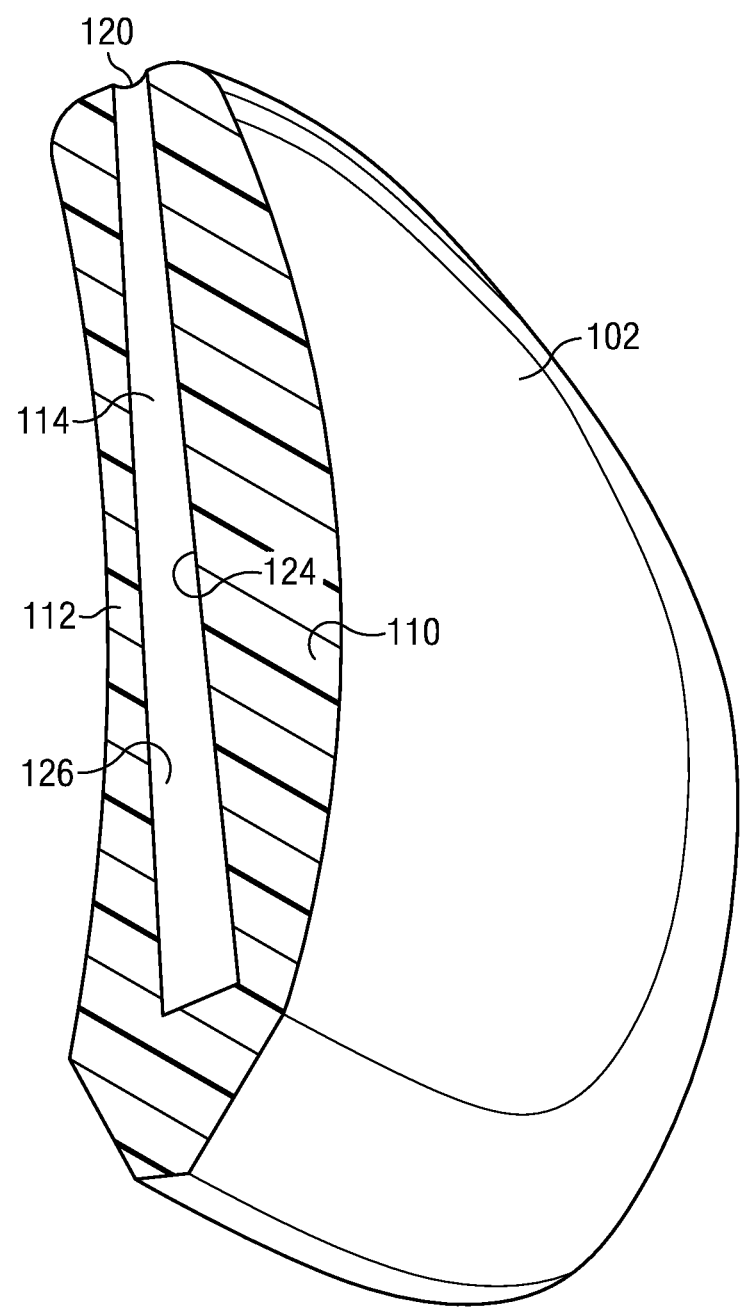
FIG. 5 is an illustration of a cross-sectional view of the flow regulating system of FIG. 3 taken along lines 5-5 in FIG. 3 according to the principles of the present disclosure.

FIGS. 3-5 show the plate 102 and drainage tube 104 of the implantable system 100 in greater detail. FIG. 3 shows an isometric view of the plate 102, FIG. 4 shows a cross-sectional view of the plate 102 taken along lines 4-4 in FIG. 3, and FIG. 5 shows a cross-sectional view of the plate 102 taken along lines 5-5 in FIG. 3.

As will be appreciated from the discussion below, the plate 102 is formed with a capillary valve having an inner chamber where capillary action is sued to regulate the amount of liquid in the valve, and thereby open and close the valve. In the embodiment described, the particular arrangement of the plate 102 provides fluid flow only when the pressure differential between atmospheric pressure, anterior chamber pressure, and drainage site pressure indicate that drainage is desirable. That is, the plate 102 may be designed so that drainage occurs when pressure differentials exceed a particular value, and drainage may not occur when pressure differentials are below the particular value.

With reference to FIGS. 3-5, the plate 102 includes a valve having a housing with an upper wall 110 and a lower wall 112. These walls 110, 112 define boundaries corresponding to inner surfaces 124, 126 of the walls 110, 112 that together define a chamber 114. In the embodiment described, the chamber 114 includes three access ports. These are an inlet port 116, an outlet port 118, and an air vent port 120. As can be seen in the embodiment shown, the inlet port 116 is in fluid communication with the drainage tube 104. Accordingly, when the valve is used as a part of drainage device that operates to regulate or control IOP, aqueous humor may flow through the drainage tube 104, through the inlet port 116, and into the chamber 114. In a similar manner, the outlet port 118 leads to a drainage site, another fluid processing system, or other location. When the valve is used as a part of drainage device to regulate or control IOP, aqueous humor may flow from the chamber 114 through the outlet port 118 to a drainage site in the patient's eye. The drainage site may be adjacent the outlet port 118 or alternatively, an additional tube, valve, or pump may be lead the fluid elsewhere for drainage. Since the air vent port 120 communicates with or is exposed to atmospheric pressure, some embodiments employ an air tube connected to the air vent port 120 that extends to location outside of the body either through the skin or through the corner of the eye lids. In other embodiments, the air vent port 120 is in fluid communication with a reference pressure representative of atmospheric pressure. Since the tube to the air vent port 120 is used to transmit air, it can be made extremely thin. In a preferred embodiment, the drainage tube diameter or lumen is sized larger that the gap height at the ports 116, 118, 120.

As in current GDDs, the drainage tube 104 entering the valve (connected to the inlet port 116 of the valve) is implanted in the anterior chamber and the plate 104 (with the outlet port 118) is implanted underneath the conjunctiva to allow aqueous flow out of the anterior chamber of the eye. Zone Name: A1,AMD In some embodiments, the plate 102 is made of hydrophobic materials. Hydrophobic materials tend to repel liquids, such as water or aqueous humor. In one example, the hydrophobic plate 102 is made of TEFLON (polytetrafluoroethylene). In other embodiments, the plate 102 comprises a hydrophobic coating, such as a TEFLON (polytetrafluoroethylene) coating, about the chamber 114, including on the inner surfaces 124, 126. Other hydrophobic materials are contemplated. In addition, modifications of the plate inner surface structures are contemplated. These may include creating microstructures in the inner surfaces by etching, increasing surface roughness by chemical processing and other methods that affect the hydrophobicity of a surface. While hydrophobic materials may be used in a preferred embodiment, other embodiments use any type of material that is capable of inducing capillary action when placed in proximity of one another. Some embodiments have an overall surface roughness less than about 5 microns, while some of these have a surface roughness less than about 1 micron.

Generally, IOP is a gauge pressure reading—the difference between the absolute pressure in the eye (as reflected in the fluid pressure at the inlet port 116) and atmospheric pressure (as reflected at the air vent port 120). Atmospheric pressure, typically about 760 mmHg, often varies in magnitude by 10 mmHg or more depending on weather conditions or indoor climate control systems. In addition, the effective atmospheric pressure can vary significantly—in excess of 200 mmHg—if a patient goes swimming, hiking, riding in an airplane, etc. Such a variation in atmospheric pressure is significant since IOP is typically in the range of about 15 mmHg Thus, for accurate regulation of IOP, the valve considers the pressure readings for the anterior chamber (at the inlet port 116) relative to atmospheric pressure in the vicinity of the eye (at the air vent port 120).

Although FIGS. 3-5 show the valve with the chamber 114 in a curved housing, some embodiments incorporate a housing formed of stacked first and second wafers or chips. Forming the valve from stacked chips or wafers may facilitate formation of the flat and planar surfaces of the chamber 114. As such, the distance of the gap in the chamber between the inner surfaces 124, 126 may be precisely controlled in order to more easily achieve the desired valve characteristics, such as a desired cracking pressure. In some embodiments, these chips may be implanted directly within the eye or may be coated and then implanted directly within the eye. In other embodiments, these may be embedded in a biocompatible outer housing configured and shaped to comfortably interface with the eye of the patient, such as having a shape shown as shown in FIG. 3, for example.

Figure 6:
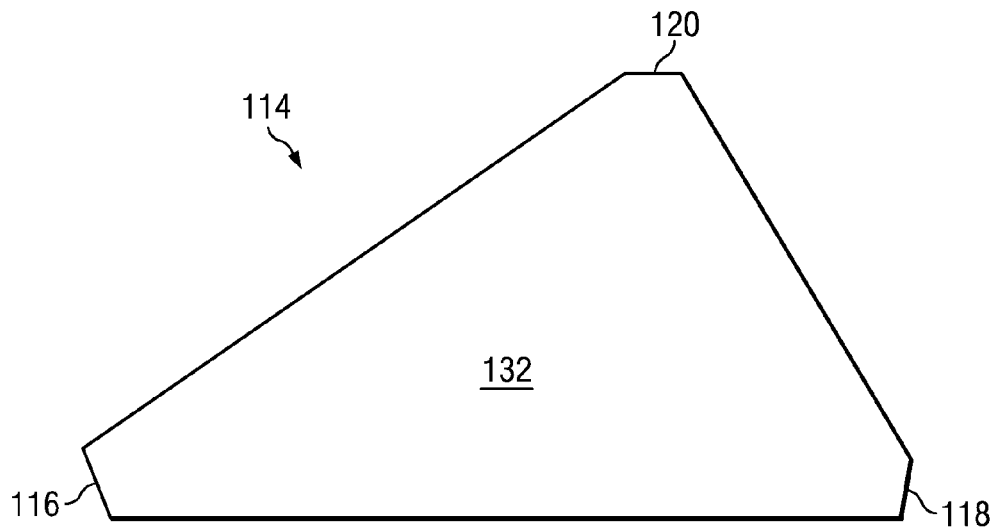
FIG. 6 is a line sketch of a top view of boundaries representing surfaces that define an exemplary chamber of the flow regulating system of FIG. 3 according to the principles of the present disclosure.
Figure 7:
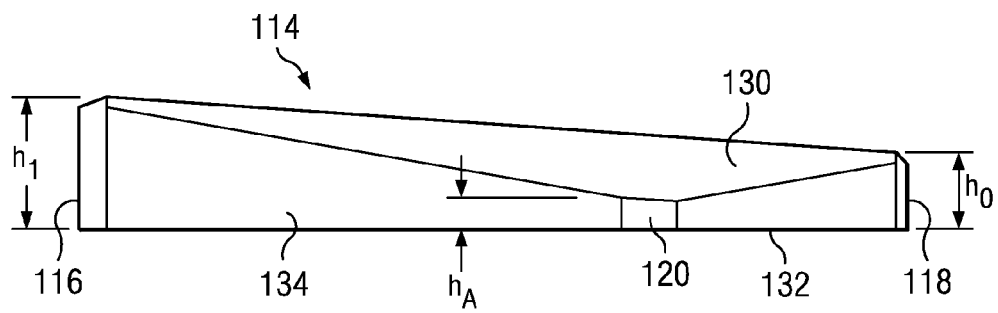
FIG. 7 is a line sketch of a side view of boundaries representing surfaces that define an exemplary chamber of the flow regulating system of FIG. 3 according to the principles of the present disclosure.

FIGS. 6 and 7 show the chamber 114 as defined by an upper boundary 130, a lower boundary 132, and side boundaries 134. The upper and lower boundaries 130, 132 correspond to inner surfaces 126, 128 that are formed by the upper wall 110 and a lower wall 112 (FIGS. 4-5). The chamber 114 is formed of a thin gap between the hydrophobic boundaries 130, 132. The gap size will vary depending on the application, but in some embodiments, may be within the range of about 2-100 microns. The size may be higher or lower depending upon the application. FIG. 6 also shows the inlet port 116, the outlet port 118, and the air vent port 120. In the embodiment shown, the chamber 114 is a triangular shape with the three ports 116, 118, 120 at the triangle vertices. The boundaries 130, 132 are, in the embodiment shown, flat, planar walls placed in a non-parallel relationship. That is the planar upper boundary 130 is angled relative to the planar lower boundary 132. The thickness of the gap forming the chamber 114 varies between the three ports, as can be seen in FIG. 7. In the embodiment shown, the gap size at the ports is referenced by $h_i$ as the gap size at the inlet port 116, $h_o$ as the gap size at the outlet port 118, and $h_a$ as the gap size at the air vent port 120. In this example, $h_i$ is greater than $h_o$, and $h_o$ is greater than $h_a$. As such, in this embodiment, $h_i > h_o > h_a$. Although other sizes are contemplated, one embodiment includes ports sizes where $h_i = 20$ microns, $h_o = 10$ microns, and $h_a = 5$ microns.

Figure 8:
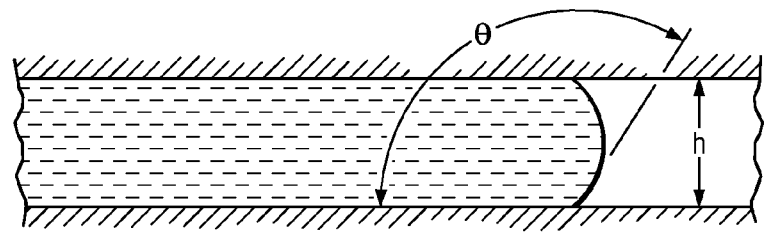
FIG. 8 is an illustration of a fluid between two hydrophobic plates showing a diagram of a contact angle.

Operation of the valve is described with reference to FIGS. 8-12. FIG. 8 shows a liquid between two hydrophobic plates in order to partially explain the operation of the capillary valve. The valve operates by means of the capillary action. The pressure difference between air and water in a thin capillary (cylinder) is commonly known. A similar equation can be derived for a water/air interface between two parallel solid surfaces:

$$pc = \frac{\gamma \cos\theta}{h} \quad (1)$$

In the equation above, h is the size of the gap between surfaces, y is the surface tension of the liquid, and θ is the contact angle. For reference, the gap h and the contact angle θ are shown in FIG. 8. The contact angle θ shown in FIG. 8 is defined by the hydrophobic or hydrophilic property of the surfaces. A hydrophilic surface θ<90° makes the pressure pc positive. That is, the pressure draws water into the gap between the surfaces. A hydrophobic surface (e.g., TEFLON (polytetrafluoroethylene) ) θ>90° makes the pressure pc negative or expels water from the gap. The water enters the valve chamber 114 from the inlet 116 where the gap is the largest. The back-up pressure (e.g., the anterior chamber pressure) of the fluid controls how far it will reach within the valve chamber 114. For a given inlet pressure p, the water will reach only the space where the gap is sufficiently wide:

$$h > -\frac{\gamma \cos\theta}{p} \quad (2)$$

As such, the thinner the gap, the higher the pressure needed to fill it with fluid. The area occupied by water at different pressures is shown in FIGS. 9-12. The cracking pressure is the pressure at which the fluid reaches the outlet port 118 and provides a path between the inlet port 116 and the outlet port 118:

$$p_{open} = \frac{\gamma \cos\theta}{h_o} \quad (3)$$

Under normal operation of the valve, the water will typically not reach the air vent port 120 opening where the gap is the thinnest. That is, the hydrophobic properties of the boundaries 130, 132 resist additional capillary action as the boundaries to converge in the direction of the air vent port 120. As such, the hydrophobicity also resists the pressure of the fluid entering the inlet port 116. Because of the hydrophobicity of the boundaries, the valve maintains an air-water interface within the valve chamber 114. The air-water interface enables the opening of the valve at a particular cracking pressure. Without the air-water interface, the valve may continue to drain without abatement once it is filled with liquid. It is also important for the application in a GDD that the outlet pressure does not affect the action of the valve. The opening pressure $p_{open}$ is the difference of inlet port pressure (anterior chamber pressure) and the air vent port pressure (atmosphere).

In some embodiments, the valve is designed to maintain the air-water interface within the valve chamber 114 when the pressure differential is between 2 and 100 mmHg In other embodiments, the valve is designed to maintain the air-water interface within the valve chamber 114 when the pressure differential is between 2 and 50 mmHg In yet other embodiments, when the pressure differential is between 2 and 40 mmHg. Other arrangements are also contemplated.

Figure 9:
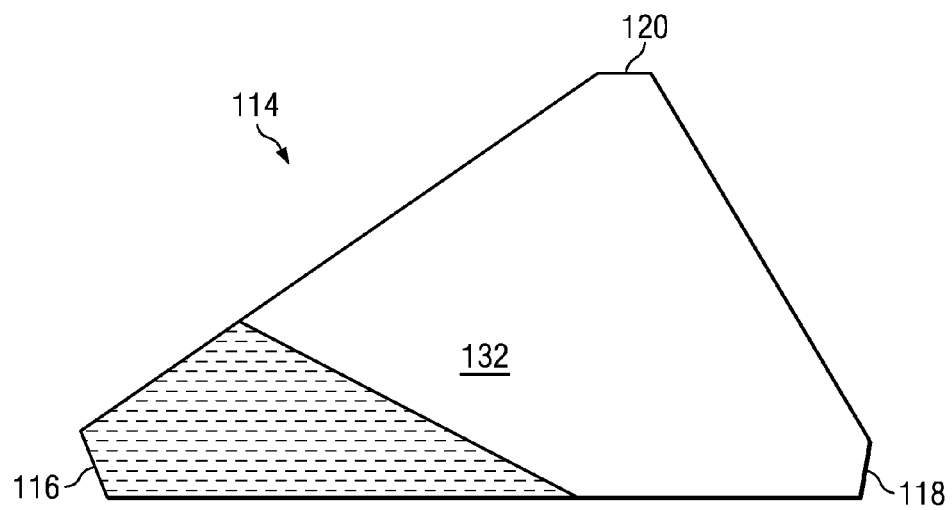
FIG. 9 is a line sketch of a top view of boundaries representing surfaces that define an exemplary chamber of the flow regulating system of FIG. 3 with fluid at a first pressure according to the principles of the present disclosure.
Figure 10:
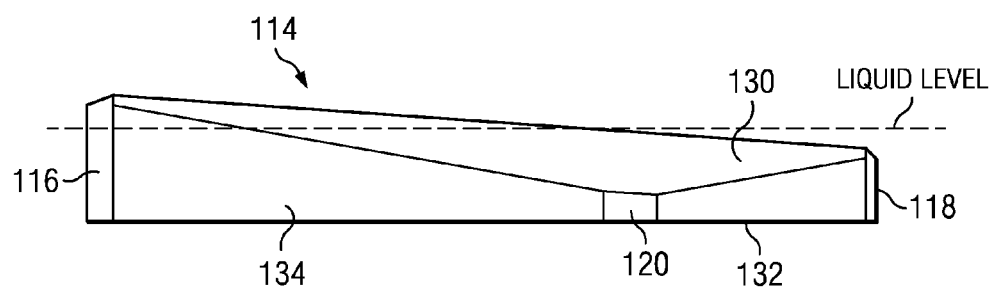
FIG. 10 is a line sketch of a side view of boundaries representing surfaces that define an exemplary chamber of the flow regulating system of FIG. 3 with fluid at a first pressure according to the principles of the present disclosure.
Figure 11:
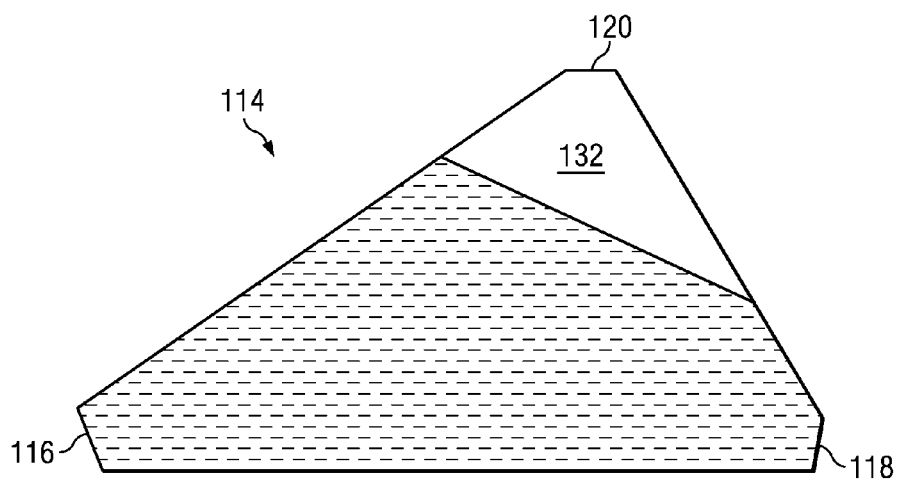
FIG. 11 is a line sketch of a top view of boundaries representing surfaces that define an exemplary chamber of the flow regulating system of FIG. 3 with fluid at a second pressure according to the principles of the present disclosure.
Figure 12:
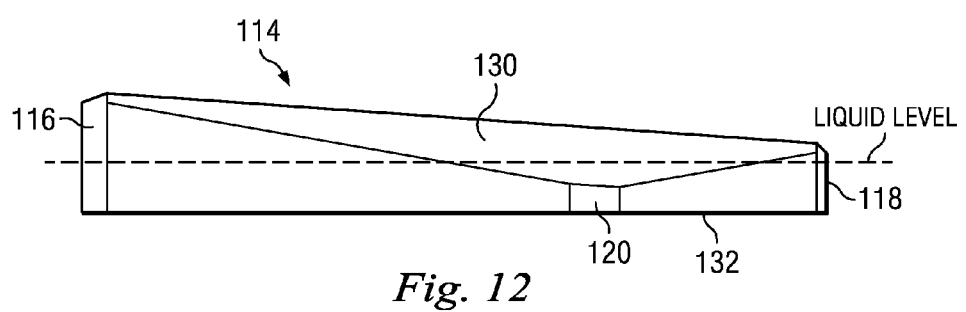
FIG. 12 is a line sketch of a side view of boundaries representing surfaces that define an exemplary chamber of the flow regulating system of FIG. 3 with fluid at a second pressure according to the principles of the present disclosure.

Operation of the exemplary valve will be described with reference to FIGS. 9-12. FIGS. 10-12 show the same boundaries as shown in FIGS. 9 and 10, but with the fluid within the chamber 114 at different levels. Zone Name: A3,AMD,M In this example shown, for purposes of explanation, the boundary walls are made from TEFLON (polytetrafluoroethylene) (θ=115°, cosθ =-0.42). In this embodiments, the gap size at the outlet port 118 is h0=10 microns, the gap size at the inlet port 116 hi=20 microns, and the gap size at the air vent port ha=5 microns. According to the equations 1-3 above, the liquid enters the valve chamber 114 when the IOP=11.5 mmHg; the valve will open at IOP=23 mmHg, and the valve will function reversibly till the IOP reaches 46 mmHg.

FIGS. 9 and 10 show the chamber boundary with water penetration at 15 mmHg, or at an IOP of 15 mmHg. Accordingly, while an IOP of 15 mmHg is sufficient to draw fluid into the chamber via capillary action, in this example, the IOP is insufficient to open the valve. Accordingly, the valve in FIGS. 9 and 10 is in a closed state by virtue of the equilibrium achieved between the atmospheric pressure and the fluid pressure at the inlet port 116. However, since the liquid is unable to flow to the outlet port 118, liquid is unable to drain through the valve. FIG. 10 shows a side view of the chamber with a fluid level within the chamber.

FIGS. 11 and 12 show the chamber boundary with water penetration at 30 mmHg, or at an IOP of 30 mmHg. As can be seen, an IOP of 30 mmHg is sufficient to draw fluid into the chamber 114 via capillary action to a depth sufficient to place the fluid in communication with not only the inlet port 116, but also the outlet port 118. Accordingly, the liquid being drawn into the chamber 114 at the entrance port is also enabled to flow out of the outlet port 118. Therefore, the valve is in an open state. FIG. 12 shows a side view of the chamber with a fluid level within the chamber. As can be seen, the fluid level has progressed within the valve a distance sufficient to reach the outlet port 118.

In one exemplary use, the implantable device 100 is used to treat an ocular condition, such as, for example, an elevated IOP. In this example, the implantable device 100 may be introduced to a patient's eye using conventional methods. A distal end of the drainage tube 104 may be inserted into the anterior chamber of the eye. In some embodiments, an atmospheric pressure tube may form a part of and/or extend from the air vent port 120 of the implant. Accordingly, in some instances, the method may include orienting an atmospheric pressure tube. This may include directing the atmospheric pressure tube to a location outside of the body either through the skin or through the corner of the eye lids. Other locations are contemplated. In some embodiments, the air vent port 120 may be communication with a separate independent air chamber that includes an air source representative of atmospheric pressure. Other embodiments do not include a separate tube extending from the air vent port.

With the implantable device 100 disposed in the eye, operation occurs as the IOP, which is a function of pressure in the eye and atmospheric pressure, fluctuates. When the IOP is below a design value of the valve, flow through the valve does not occur. This is because the equilibrium reached at the air-liquid interface between the capillary action of the valve and the pressure differentials occurs at a location where the inlet and outlet ports are not in fluid communication. As such, the valve is in a closed state.

As IOP increases, the fluid level within the valve increases, working against the resistance to movement offered by the hydrophobic walls and the atmospheric pressure. At a designed cracking pressure, the fluid level ultimately reaches the outlet port 118, placing the inlet and outlet ports 116, 118 in fluid communication. Accordingly, fluid flow may occur through the valve. As the IOP decreases as a result of the drainage relief, the fluid level in the valve decreases below the cracking pressure and further fluid flow is prevented. In some embodiments, the valve is designed to have a cracking pressure at a pressure differential less than about 50 mmHg. In other embodiments, the valve has a cracking pressure at a pressure differential less than about 40 mmHg. In other embodiments, the valve has a cracking pressure at a pressure differential less than about 30 mmHg. In other embodiments, the valve has a cracking pressure at a pressure differential less than about 20 mmHg In other embodiments, the valve has a cracking pressure within a range of about 5 and 30 mmHg. Other ranges and limits are contemplated.

The design described herein may be both reliable and durable, as it is simple and has no moving parts. Accordingly, in some environments, it may have a useful life longer than other valves. In addition, because of its simple design, it may be relatively inexpensive to manufacture and implement. Furthermore, it may be predictable, and may be designed fairly accurately to open and close at designated pressures. Furthermore, since it has no moving parts, extended use may not result in degradation or wear that would otherwise change the responsiveness or accuracy of the valve. It is also simple to design to achieve desired cracking pressures. Accordingly, the valve disclosed herein provides multiple benefits to the user and the designer.

Although described with reference to an implantable device for the treatment of an ocular condition, such as elevated IOP, the valve described herein may be used in many other applications both in the medical industry and outside the medical industry. For example, it may be used in drug delivery applications, in fluid lubricating applications, in cooling operations, in microfluidics operations, including controlling flows on etched microfluidic chips, and in other industries and applications. In addition, the valve may be used as a pressure relief valve and, in some embodiments, is disposable. It may find particular utility in micro-fluidic applications requiring over-pressure protection. In addition, it may be used as a sensor forming a part of a mechanical feedback in a closed-loop system. This may, for example, be useful in micro-fluidic applications. In such applications, the valve may be calibrated to check the water level based on pressure and hence may be used, for example, as feedback for controlling the speed on a micro pump. The valve may also find utility in controlling flows in lab on a chip technologies. Yet other applications would be apparent to one of skill in the art.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

What is claimed is:

1. A capillary fluid flow valve, comprising:
a chamber having a first boundary surface and a second boundary surface defined by a housing, the first and second boundary surfaces being spaced apart by a gap sized to invoke capillary action between the surfaces, the first surface being angled relative to the second surface, the chamber having an inlet port, an outlet port, and an air vent port, wherein the gap at the air vent port is smaller than the gap at the outlet port and the gap at the outlet port is smaller than the gap at the inlet port; wherein the chamber is triangular, and the inlet port, outlet port, and air vent port are disposed at the vertices of the triangular chamber.

2. The fluid flow valve of claim 1, wherein the opposing surfaces are hydrophobic surfaces.

3. The fluid flow valve of claim 2, wherein the opposing surfaces are formed of polytetrafluoroethylene.

4. The fluid flow valve of claim 1, wherein the air vent port is open to atmospheric pressure.

5. The fluid flow valve of claim 1, wherein the surfaces are configured to maintain an air to liquid interface within the chamber when the pressure differentials are less than 100 mmHg.

6. The fluid flow valve of claim 1, wherein the inlet port and the outlet port are spaced apart so that a cracking pressure for the valve is less than 50 mmHg.

7. The fluid flow valve of claim 1, wherein the surfaces are angled to resist ingress of fluid toward the air vent port.

8. The fluid flow valve of claim 1, wherein the surfaces are planar surfaces having a surface roughness less than five microns.

* * * * *